United States Patent
Klein et al.

(10) Patent No.: US 8,105,257 B2
(45) Date of Patent: Jan. 31, 2012

(54) EXTREMITY STRESS ATTENUATION MODALITY WITH RESISTANCE-MECHANISM ENGAGING MEMBER

(75) Inventors: Erin Klein, Oaklawn, IL (US); Ryan Crews, Buffalo Grove, IL (US); Stephanie Wu, Gurnee, IL (US); David G. Armstrong, Green Oaks, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 11/541,490

(22) Filed: Sep. 29, 2006

(65) Prior Publication Data
US 2007/0203440 A1 Aug. 30, 2007

Related U.S. Application Data (60) Provisional application No. 60/722,291, filed on Sep. 30, 2005.

(51) Int. Cl.
*A61F 5/00* (2006.01)

(52) U.S. Cl. ............................................ 602/23; 602/27
(58) Field of Classification Search ................ 602/5, 16, 602/20–23, 26–28; 128/882
See application file for complete search history.

(56) References Cited

U.S. PATENT DOCUMENTS

| 2,558,986 A | * | 7/1951 | Seelert ............................ 602/16 |
| 4,494,534 A | * | 1/1985 | Hutson ............................ 602/16 |
| 5,014,690 A | * | 5/1991 | Hepburn et al. ................. 602/16 |
| 5,971,946 A | * | 10/1999 | Quinn et al. .................... 602/27 |

* cited by examiner

*Primary Examiner* — Michael A. Brown
(74) *Attorney, Agent, or Firm* — Joseph A. Fuchs; Rockey, Depke & Lyons, LLC (57) ABSTRACT

The present invention provides an extremity stress reducing modality for a human subject having an extremity, the extremity having an uninjured portion and an injured portion. The modality includes: (1) a frame having a connecting member for removably connecting the frame to an extremity of a human subject; (2) a support member on the frame for engaging the uninjured portion but not the injured portion; and (3) an attachment member on the frame for attaching the frame to a portion of a moveable resistance mechanism.

22 Claims, 10 Drawing Sheets

FIG. 12
Contact Area – Left Foot

FIG. 13
Contact Area – Right Foot

FIG. 14
Peak Pressure (kPa) – Left Foot

FIG. 15
Peak Pressure (kPa) – Right Foot

FIG. 16
Pressure Time Integral (N*s) – Left Foot

FIG. 17
Pressure Time Integral (N*s) – Right Foot

EXTREMITY STRESS ATTENUATION MODALITY WITH RESISTANCE-MECHANISM ENGAGING MEMBER

CROSS-REFERENCE TO RELATED APPLICATION

This application claims priority to U.S. Provisional patent application Ser. No. 60/722,291 filed on Sep. 30, 2005, which is incorporated herein by reference in its entirety and made a part hereof.

FEDERALLY SPONSORED RESEARCH OR DEVELOPMENT

Not Applicable.

BACKGROUND OF THE INVENTION

Diabetes mellitus has become a growing health concern over the past two decades. In the years between 1980 and 2002, the number of people in the United States who have been diagnosed as having diabetes rose from 5.8 million to 13.3 million. Additionally, it was estimated by the Center of Disease Control (CDC) that there were 5.2 million unreported cases in 2002, thereby yielding a total of over 18 million Americans with diabetes.

Diabetes mellitus is a condition where the affected person has either a shortage or complete lack of insulin. This insulin insufficiency leads to high circulating levels of glucose and fatty acids in the blood. Increased blood glucose levels can cause many health problems which include heart disease, stroke, blindness, kidney failure, pregnancy complications, lower extremity amputations and peripheral neuropathy.

The resultant lack of sensation on the plantar aspect of the foot due to peripheral neuropathy often leads to the development of cutaneous ulcerations on the foot. Diabetic foot ulcerations are a serious medical concern. They have been shown to cause substantial emotional, physical, productivity and financial losses. The most costly and feared consequence of a foot ulcer is limb amputation, which occurs 10 to 30 times more often in patients with diabetes than the general population.

An important observation to note is that while the incidence of diabetes mellitus has been increasing in the United States, so has the rate of obesity. Many researchers and epidemiologists believe that insulin resistance (leading to diabetes mellitus type 2), obesity (especially in the abdomen), dyslipidemia, and hypertension have a common underlying cause given that they often occur together as the "Deadly Quartet."

Leading a sedentary lifestyle is a major contributor to obesity. In addition to reducing obesity, an increase in physical activity may help heal diabetic foot ulcers. Physical activity increases angiogenesis, a necessary process for healing that is stunted in persons with diabetes. The activation in muscles also increases tissue temperature. Increasing tissue temperature through exercise may yield similar benefits as thermotherapy, a proven method for helping wounds to heal.

Besides helping to heal existing diabetic foot ulcers, exercise may help prevent future occurrences. Exercise physiologists and the CDC have documented the effects of physical activity and exercise on hypertension, blood glucose and dyslipidemia. The overall conclusion is that regular exercise (as defined by the American College of Sports Medicine) results in similar trends in blood pressure, heart rate, blood lipid levels and resting blood glucose levels. Decreasing blood glucose levels in persons with diabetic foot ulcers may delay the progression of neuropathy which may in turn decrease the incidence of future ulceration.

SUMMARY OF THE INVENTION

The present invention provides an extremity stress reducing modality for a human subject having an extremity, the extremity having an uninjured portion and an injured portion. The modality includes: (1) a frame having a connecting member for removably connecting the frame to an extremity of a human subject; (2) a support member on the frame for engaging the uninjured portion but not the injured portion; and (3) an attachment member on the frame for attaching the frame to a portion of a moveable resistance mechanism.

The present invention further provides a foot gear for off-loading a forefoot of a human subject during a resistance exercise including: (1) a cleat dimensioned to support a rearfoot of a human subject and to allow a forefoot of the subject to protrude freely with no fixed base beneath the forefoot; (2) a leg support portion adapted to receive a leg of the subject, the leg support portion including a pair of spaced vertical arms connected to opposed lateral edges of the cleat so as (a) to extend upwardly past sides of an ankle of a human subject and terminating adjacent sides of a calf of a human subject and (b) to support the ankle at approximately 90 degrees to the foot gear; (3) an attaching member on the foot gear for securing the foot gear to the leg of the subject; and (4) a securing member on the foot gear to connect the foot gear to a moveable resistance mechanism.

The present invention further provides an extremity stress reducing modality assembly for a foot of a human subject. The assembly includes: (1) a frame having a connecting member for removably connecting the frame to a foot of a human subject; (2) a support member on the frame for engaging a rearfoot portion of the foot while leaving a forefoot portion of the foot unsupported; (3) a resistance member under tension and capable of rotational or translational motion; and (4) an attachment member on the frame for attaching the frame to the resistance member.

The present invention further provides a method for using an extremity stress reducing modality for a human subject having an extremity having an injured portion and an uninjured portion. The method includes: (1) providing a frame having a connecting member for removably connecting the frame to an extremity of a human subject, a support member on the frame for engaging the uninjured portion but not the injured portion; and an attachment member on the frame for attaching the frame to a portion of a moveable resistance mechanism; (2) providing a resistance device having a resistance member under tension and is moveable upon application of pressure to move rotationally or translationally; (3) connecting the frame to the extremity of a human subject with the uninjured portion being supported by the support member and the injured portion not being supported by the support member; and (4) attaching the frame to the resistance member.

BRIEF DESCRIPTION OF THE DRAWINGS

FIG. 9 A, B, C are respectively three dimensional diagrams indicating pressure in a participants foot in a study including (A) control where no cleat was worn, (B) a cleat with a shoe and (C) a cleat with an insole and no shoe

DETAILED DESCRIPTION OF THE INVENTION

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

The present invention provides an extremity stress reducing modality for a human subject having an extremity, the extremity having an uninjured portion and an injured portion. The modality includes: (1) a frame having a connecting member for removably connecting the frame to an extremity of a human subject; (2) a support member on the frame for engaging the uninjured portion but not the injured portion; and (3) an attachment member on the frame for attaching the frame to a portion of a moveable resistance mechanism. While the modality will be discussed below in detail in the context of a leg and foot engaging modality it should be understood that it is envisioned by the inventors of the present invention of providing extremity engaging modalities for other extremities such as arms, hands, finger and toes. Further, the present invention contemplates using the modality to allow resistance exercises of any type and particularly exercises requiring moving a resistance member under tension. The movement of the resistance member can be of any type including rotational motion, translational motion or other. The translational motion can be vertical, horizontal, along a line transverse to vertical or horizontal or a combination of any of these types of translational motions.

Figure 1:
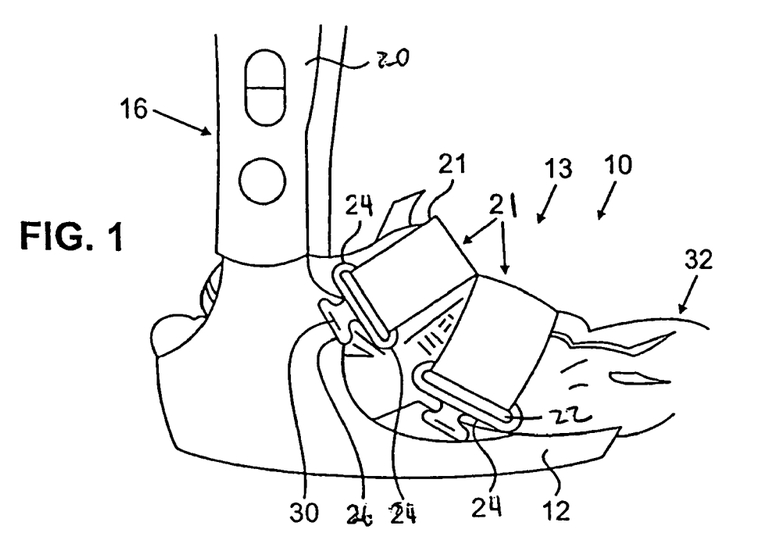
FIG. 1 is a side elevation view of a foot stress reducing modality holding a gym shoe.

FIG. 1 shows a foot and leg resistance attenuating modality which will sometimes be referred to as foot gear 10. The foot gear 10 offloads a forefoot of a human subject during a resistance exercise such as a cycling exercise routine. Such foot gear 10 can be used by diabetic patients having an ulcer on their forefoot. The foot gear 10 is similar in design to a short leg walker except that the foot gear of the present invention has a support or cleat 12 which is truncated at approximately between a rearfoot portion and a forefoot portion (i.e., at the midfoot) such that when worn by a human subject the rearfoot of the human subject is supported by the cleat and the forefoot is allowed to protrude freely beyond the cleat with no fixed base beneath the forefoot.

Figure 3:
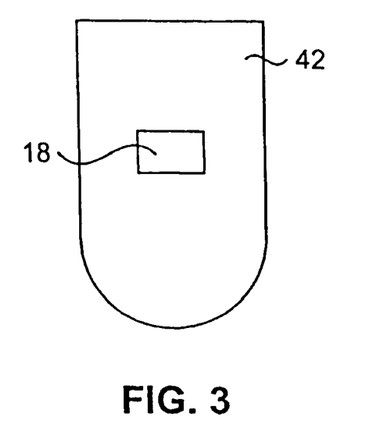
FIG. 3 is a bottom view of the cleat of FIG. 1 having a member for engaging a resistance mechanism positioned on a bottom surface of the cleat.
Figure 4:
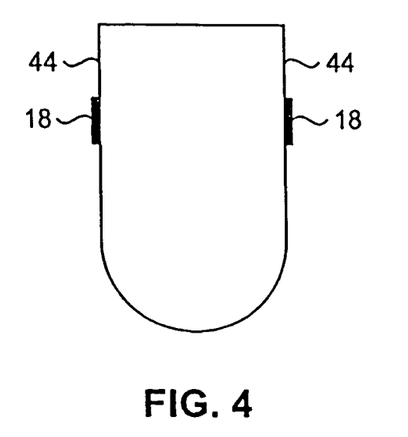
FIG. 4 is a bottom view of an alternative embodiment of the cleat of FIG. 1 having a member for engaging a resistance mechanism positioned on opposed lateral edges of the cleat.
Figure 7:
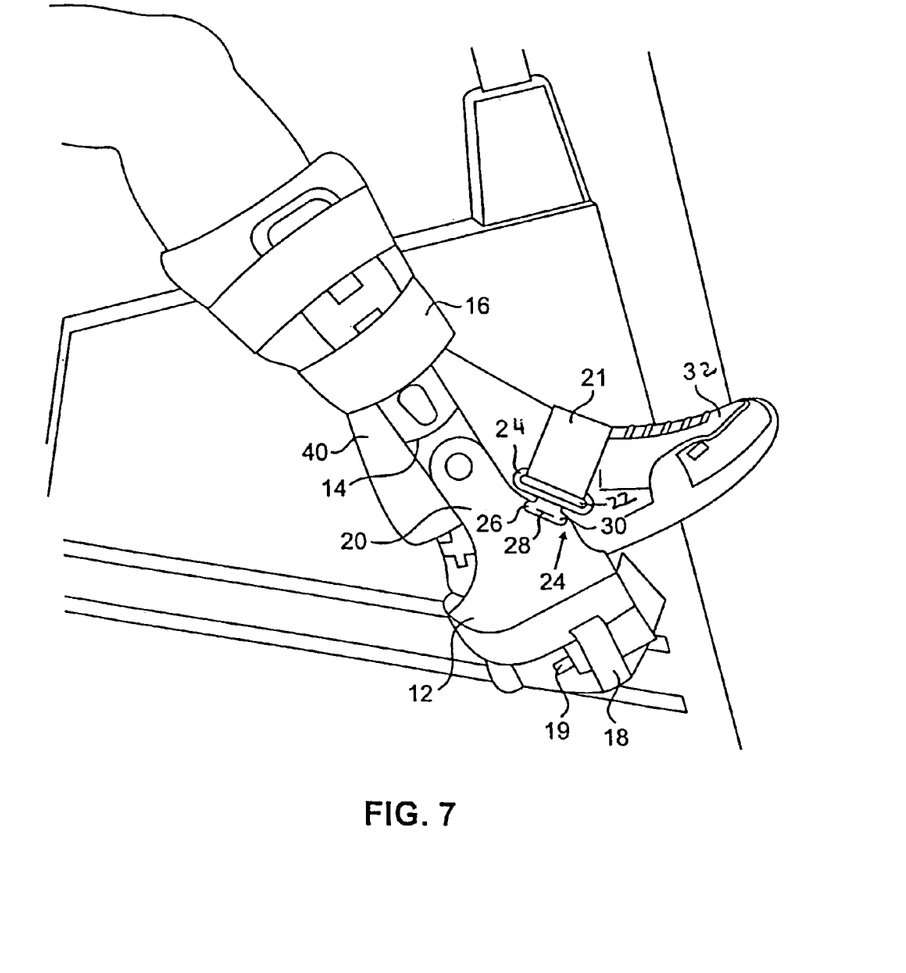
FIG. 7 is a side view of a human leg wearing a shoe and a foot gear with the foot gear engaging a resistance member in the form of a stationary bicycle pedal.

The foot gear 10 has a frame 14, a member 16 for connecting the frame to the leg of a human subject and a member 18 (FIGS. 3, 4, and 7) for connecting the frame to a resistance member 19 under tension such as the pedal of a bicycle (FIG. 7). In one preferred embodiment, the frame 14 has two vertically extending legs 20 extending from opposed lateral edges of the cleat 12. The spaced vertical legs 20 are preferably dimensioned to extend upwardly past lateral sides of an ankle of the human subject and terminate adjacent sides of a calf of the human subject. When attached to the leg of the human subject, in a preferred form of the invention, the ankle will be fixed at approximately 90 degrees to the vertical legs 20 of the foot gear. The frame 14 can be fabricated from any material suitable for its purpose including polymeric material, metals, composite material, leather, canvas, synthetic or natural rubber, carbon fiber, graphite, cellulosic, woven and non-woven fabric, and paper board. Suitable polymeric materials include both thermoplastic and thermosetting polymers and can include blends of the polymeric materials or single or multiple layer structures including the polymeric material. Suitable polymers include homopolymers, copolymers and terpolymers formed from monomers selected from substituted and non-substitued, olefins, acrylates, amides, imides, ethers, esters, carbonates, urethanes, carbonyls, ketones, aldehydes, styrenes, nitrites, dienes, vinyl chloride, vinyl alcohols, vinyl esters, vinylidene chloride, norbornene and the like. The frame can be formed using standard polymer processing techniques such as injection molding, thermoforming, extrusion, coextrusion, blow molding or other techniques well known to those skilled in the art. The frame can be formed in a single part or in separate parts and assembled using snap fittings, adhesives, solvent bonding, direct or indirect thermal welding, vibration bonding, sonic welding or other techniques well known to those skilled in the art.

In one preferred form of the invention the member for connecting the frame to a leg of the human subject include a member for securing the frame about the leg of the human and about the foot of the human. Suitable connecting members 16 include length adjustable straps 21 extending through guides 22 defined by buckles 24 located on opposed portions of the frame. The buckles 24 are secured to a portion of the frame, and in a preferred form of the invention, the buckles have a tab 26 extending therefrom with an through hole 28 to fixedly or releasably engage a boss 30 extending from an outer surface of one of the vertically extending legs 20. The straps 21, in a preferred form of the invention, have on one surface hook and loop type fasteners such that when a leading edge of the straps are directed in one direction through the guides 22 and double backed in an opposite direction, the hook and loop type fasteners on an upper strap has its hook and loop fasteners facing downward and has a second leg of the strap with its hook and loop fasteners facing upward. The downward and upward facing straps are brought into cooperative engagement with one another to releasably connect these strap portions and to form a snug fit between the frame and a foot or leg of the wearer. The hook and loop fasteners can be integrally formed on the straps or provided on a separate hook and loop fastener material and attached to the straps by an adhesive. It is also contemplated providing hook and loop fasteners on portions of the frame to allow for securing the straps directly to the frame. The hook and loop fasteners can be integrally molded onto the frame or applied as a separate strip of material using adhesives or the like.

Figure 2:
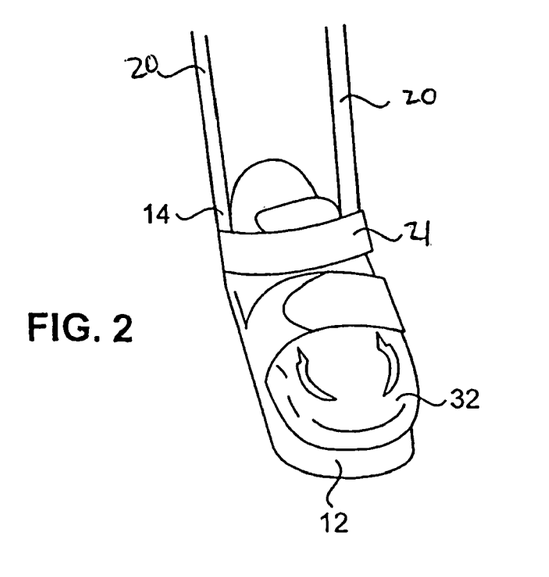
FIG. 2 is a perspective view of the cleat of FIG. 1.
Figure 6:
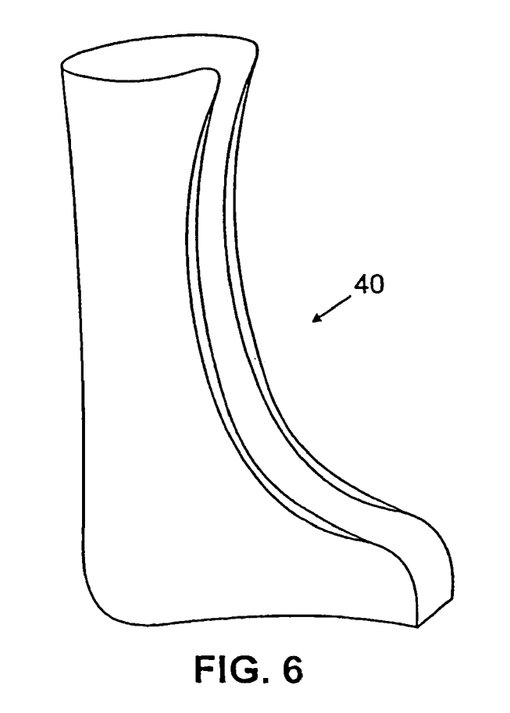
FIG. 6 is a side view of a removeable, breathable liner.

The cleat 12 and foot gear can be dimensioned to receive a human foot wearing a shoe 32 as shown in FIGS. 1, 2 and 7 or a human foot without a shoe. In a preferred form of the invention, if a shoe is not worn by the human subject, an insole insert 34 will be placed on a top surface of the cleat 12. It is also contemplated utilizing an optional breathable, foam liner 40 (FIG. 6) that is wrapped about the leg and foot of the wearer to provide comfort and protection from the frame material. Such breathable liners are well known in the art and can be fabricated from woven and nonwoven fabrics.

The resistance connecting member 18 for connecting the frame 14 to resistance member 19 can be provided in any suitable location on the frame 14 such as on a bottom surface 42 (FIG. 3) or on one or both lateral edges 42 of the cleat. The connecting member 18 can also be positioned or attached to the vertical arms of the frame. It is also contemplated that the straps can be connected to the resistance member and attach to the resistance connecting member 18. Suitable connecting members 18 can include those well known to those skilled in the art that releasably attach or fixedly attach the frame 14 to the resistance member 19 such as straps, mating interlocks on the pedal, such as those found on cleated cycling shoes and corresponding pedal, and the like. The present invention further contemplates an assembly of the frame 14 attached to the resistance member 18. To utilize such an assembly the assembly would be attached to a resistance providing mechanism, such as a stationary bicycle, and to the human subject.

The present invention further provides a method for using the foot gear 10 by a human subject to perform exercises based on a resistance providing mechanism such as an exercise bike, and especially a human subject having an extremity with a portion of the extremity being uninjured and another portion of the extremity having an injury. What is meant by an injury is a disruption in the skin such as an ulceration, blister or other similar injury and more preferably to ulcerations secondary to diabetes, and particularly those type of injuries common to the forefoot of a diabetic patient.

While the foot gear is shown in use with a pedal of a bicycle it should be understood the foot gear could be adapted to work with other resistance providing mechanisms, devices or equipment where tension is provided by weights, springs, a band, a flexible arm such as on a BOW FLEX® type equipment, a weighted fly wheel (such as on a stationary bicycle or spin bike), a fan wheel, a piston, a gear or a shuttle that moves along a track under a variable friction load. The resistance member is typically associated with a tension providing member and is moveable either rotationally or vertical or horizontal translational motion (or on a slant which is a combination of both vertical and horizontal translational motions). Use of the foot gear, as shown in the example below, is to speed the healing process of an ulcer on the forefoot of a diabetic patient and to provide other health benefits to the patient from the exercise.

EXAMPLE

Diabetic foot ulcers are the most common reason for hospital admission for people with diabetes in the United States and other nations, accounting for some 25% of hospital admissions in this population. The most costly and feared consequence of a foot ulcer is limb amputation, which occurs 10 to 45 times more often in patients with diabetes than the general population. The etiology of diabetic foot ulcerations is commonly associated with the presence of peripheral neuropathy and repetitive trauma resulting from the repetitive application of moderate to high pressure to the feet during normal weight bearing activities such as walking. Pressure mitigation has, therefore, been the focus in the treatment paradigm for diabetic foot ulcers.

Many persons with type 2 diabetes tend to lead a rather sedentary lifestyle with this inactivity being further compounded by the formation of diabetic foot ulcers. By clinical convention, patients with foot ulcers are told to reduce or eliminate weight-bearing activity until their wounds heal, which creates a vicious cycle of cardiac decompensation, weight gain and increased blood glucose levels. Weight gain adds to plantar foot pressure while the increases in blood glucose slow wound healing and impair immunity. Exercise regimens that present nominal risk to diabetic foot ulcers by imparting nominal pressure/stress to the site of the ulcers are needed to prevent the prescription of sedentary lifestyles. In addition to cardiovascular and metabolic benefits, an increase in physical activity that minimizes pressure to the foot may, in fact, help heal diabetic foot ulcers. Along with decreasing blood sugars, physical activity increases angiogenesis, a necessary component in healing that is impaired in persons with diabetes. The activation of muscles during physical activity also increases tissue temperature and may yield similar benefits as thermotherapy, a proven method for helping wounds to heal.

Besides helping to heal present diabetic foot ulcers, exercise may also help prevent future occurrences. Exercise physiologists and the CDC have documented that regular exercise (as defined by the American College of Sports Medicine) leads to decreased resting heart rate, decreased resting blood pressure, decreased blood lipid level and a more favorable resting blood glucose level. In addition, moderate physical activity (as defined by the American College of Sports Medicine) results in similar trends in blood pressure, heart rate, blood lipid levels and resting blood glucose levels. Decreasing high blood glucose levels in persons with diabetic foot ulcers may also delay the progression of neuropathy which may in turn decrease the incidence of future ulceration.

Exercise and physical activity have not been well studied in persons with or at high risk for diabetic foot ulcers primarily because there are currently no known devices available that allow patients to exercise while concomitantly mitigating pressure from the ulcer site. Accordingly, the foot gear 10 described in detail above was tested on human subjects who participated in a cycling exercise program that offloaded pressure in the forefoot.

Ten healthy adult subjects were recruited for this study. Subjects were excluded from participating if they were being treated for any chronic conditions including but not limited to coronary heart disease, congestive heart failure, diabetes mellitus (type 1 and type 2), chronic obstructive pulmonary disease or chronic bronchitis.

Each subject completed one study visit and read and signed an Institutional Review Board approved informed consent form, then completed a health screening questionnaire before commencing participation in this study.

Figure 5:
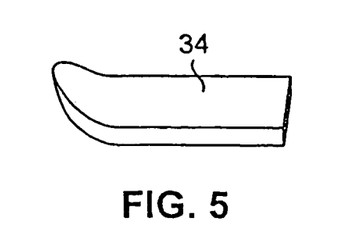
FIG. 5 is a side view of an insole.

Each participant was fit for proper sized pressure sensing insoles (Pedar X, Novel, Munich, Germany). Utilizing a stationary recumbent bicycle (Lifecycle 9500R), each participant cycled with their right foot under three different conditions: a control condition with standard Lifestyle 9500R pedals and gym shoes (Control), gym shoes in collaboration with the foot gear (GS) and an offloading insole (FIG. 5) in collaboration with the foot gear (OIC). The left foot utilized the standard pedal with a gym shoe in all trials.

The order of conditions was randomly assigned for each participant. In order to ensure the work load within each subject was consistent across the conditions, the resistance level and cadence (a range ±2 from target RPM allowed) were fixed. Resistance and cadence values were established for each subject during a warm-up period, during which subjects were instructed to cycle at a comfortable cadence and resistance.

In each condition, the participant cycled for seven consecutive minutes to ensure that fatigue was not a factor in the pedaling style of the second and third trials. Peak pressure, maximum force, contact area and the pressure-time integral were sampled at 50 Hz for 10 seconds at the end of each minute (PedarX, Novel, Munich, Germany). Heart rate and revolutions per minute were also recorded at the end of every minute.

Figure 9A:
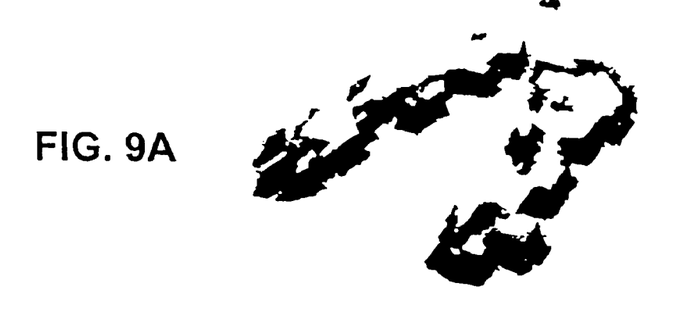
Figure 9B:
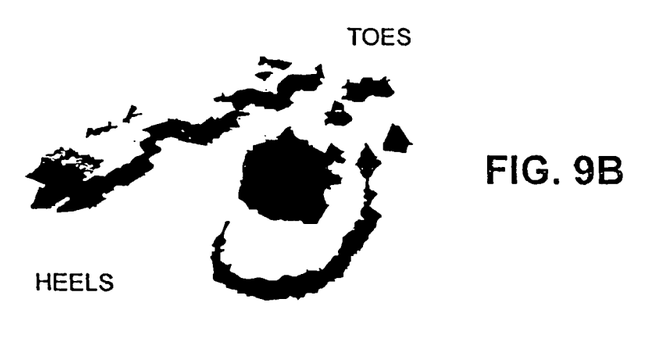
Figure 9C:
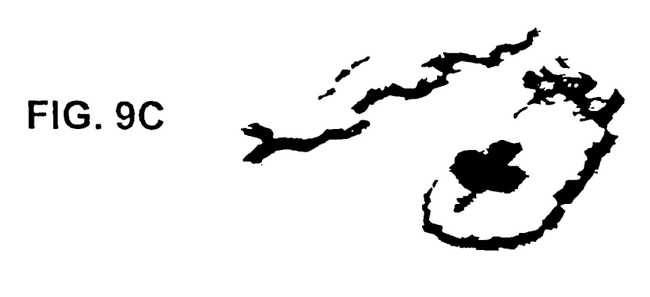

The foot was divided into two parts for data analysis: the forefoot mask and the rearfoot mask. The forefoot mask included the distal seven rows (regardless of size, each insole had an equivalent number of rows) of sensors on each insole. For nine of the ten participants, this mask measured data distal to the bases of the metatarsals. The rearfoot mask included the proximal eight rows of sensors on each insole. For nine out of ten participants, this mask measured data of the anatomical midfoot and rearfoot. (FIGS. 9 A, B, C)

In order to assess effort, percent maximum age predicted heart rate (MHR %) was compared across the three cycling conditions. In order to ensure steady state values were assessed, $7^{th}$ minute MHR % values were used for analysis. A repeated measures analysis of variance (ANOVA) compared MHR % between the cycling conditions. The contact area, peak pressure, and pressure-time integral data sets were each subjected to a 2×3×7 repeated measures ANOVA. Main effects included foot, cycling condition, and the repeated effect of sample time (1 min-7 min). Tukey's Honestly Significant Difference (HSD) Test was used for post hoc analysis of significant main effects and interactions.

The MHR % did not significantly differ ($p>0.05$) between the three conditions.

Figure 8:
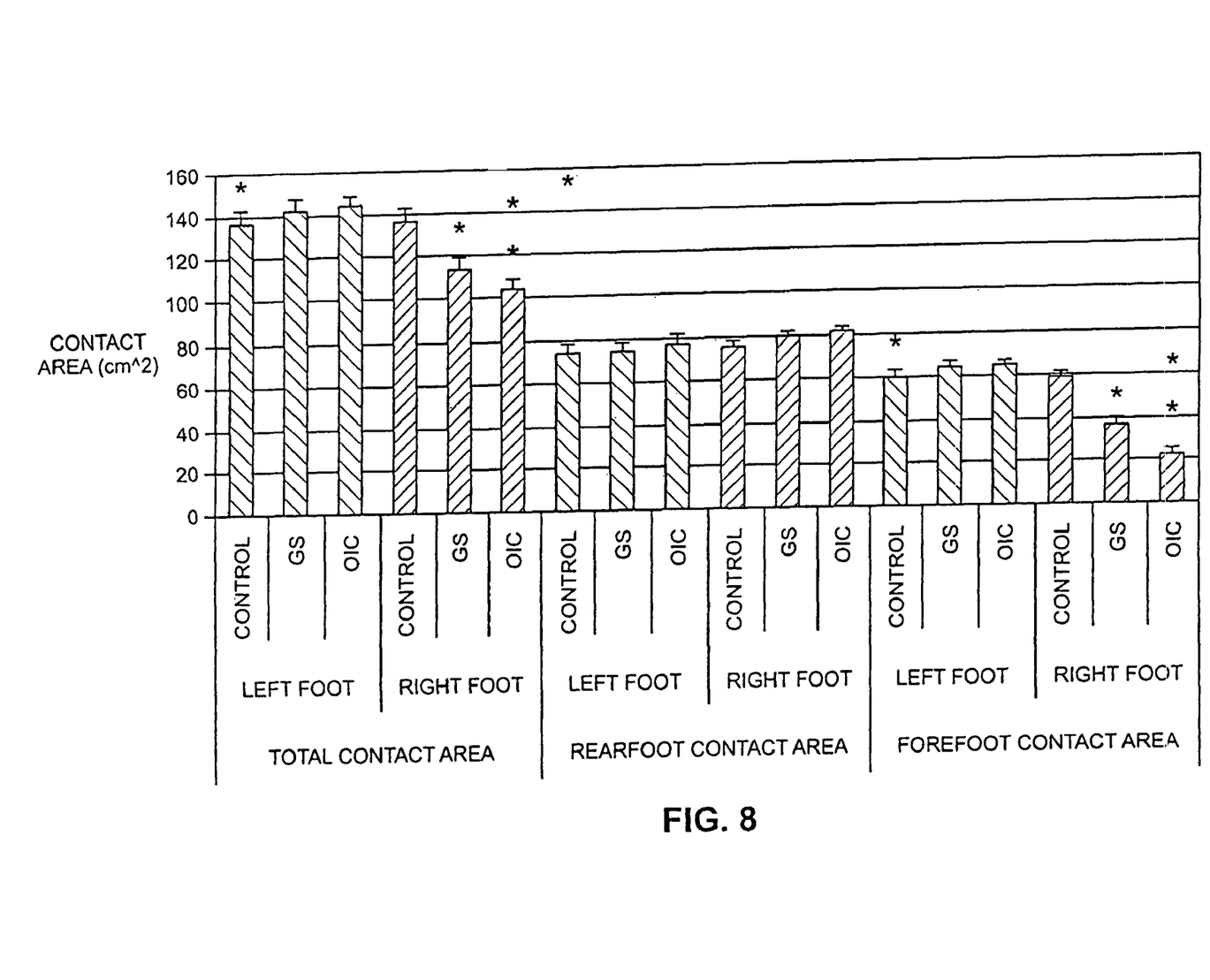
FIG. 8 is a bar graph of the results of a study showing a comparison of the contact area of the forefoot of participants wearing on their right foot a shoe (Control), a cleat and a shoe (GS) and a cleat and an insole (OIC).

The main effects of foot and cycling condition along with the interaction of foot x cycling condition were found to be significant ($p<0.01$). The left foot ($62.6\pm2.5$ cm$^2$) yielded a significantly higher contact area than the right foot ($42.5\pm4.0$ cm$^2$). A Tukey's HSD post hoc was performed to analyze the simple effect of cycling condition within foot (FIG. 8). Contact area for the left foot Control condition ($59.9\pm3.2$ cm$^2$) was lower ($p<0.01$) than either the GS ($63.5\pm2.8$ cm$^2$) or OIC ($64.2\pm2.4$ cm$^2$). Contact area for the right foot was lower ($p<0.01$) in the OIC condition ($26.1\pm5.3$ cm$^2$) than GS ($40.1\pm4.8$ cm$^2$) which was lower ($p<0.01$) than Control ($61.6\pm3.2$ cm$^2$). (FIG. 8)

None of the main effects nor interactions were found to be significant.

The main effects of foot and cycling condition along with the interaction of foot x cycling condition were found to be significant ($p=0.013$. $p=0.022$. $p<0.01$). The left foot ($139\pm4.8$ cm$^2$) yielded a significantly higher contact area than the right foot ($123\pm7.0$ cm$^2$). A Tukey's HSD post hoc was performed to analyze the simple effect of cycling condition within foot (FIG. 8). Contact area for the left foot C condition ($135.7\pm5.6$ cm$^2$) was lower ($p<0.01$) than either the GS ($139\pm5.1$ cm$^2$) or OIC ($142\pm4.3$ cm$^2$). Contact area for the right foot was lower ($p<0.01$) in the OIC condition ($110\pm7.9$ cm$^2$) than GS ($118\pm7.3$ cm$^2$) which was lower ($p<0.01$) than C ($139\pm7.1$ cm 2). (FIG. 8)

Figure 10:
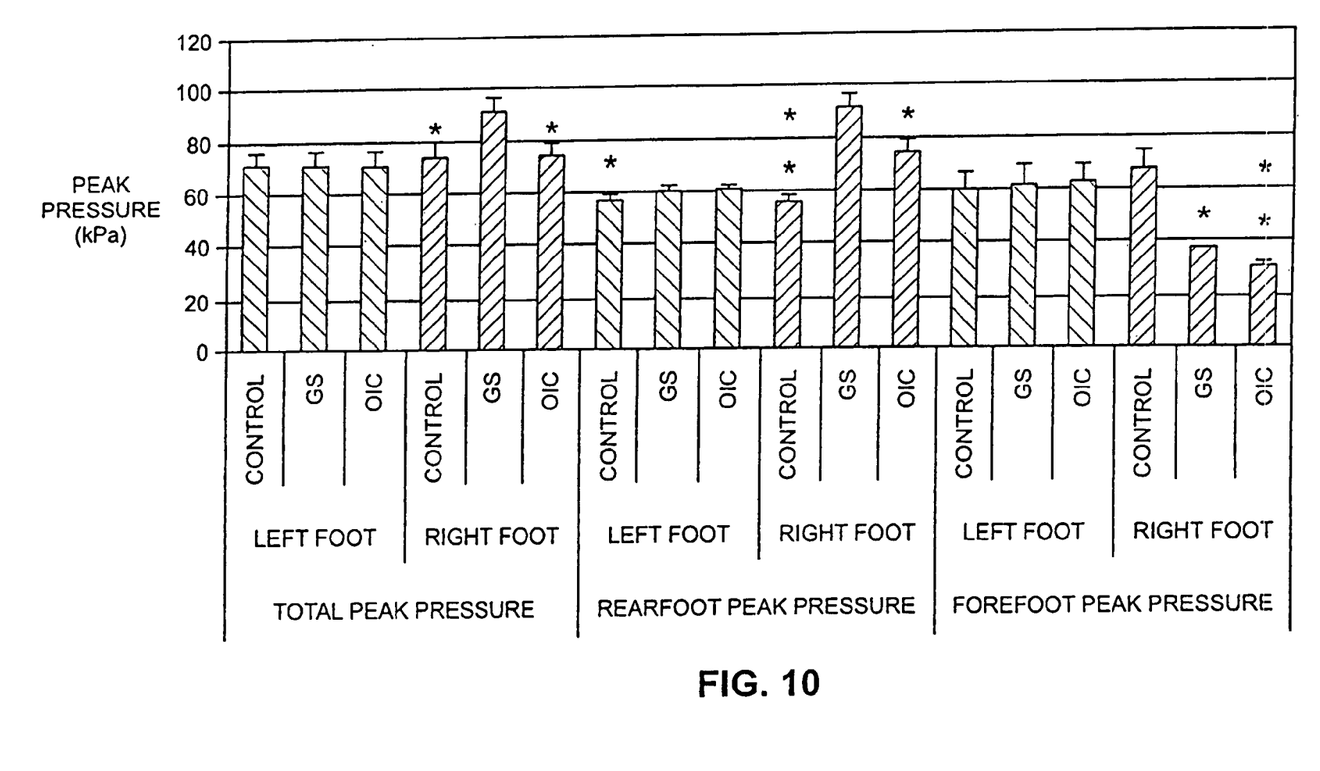
FIG. 10 is a bar graph of the results of a study showing a comparison of the peak pressure of a left foot and a right foot of participants wearing a shoe on their left foot and on their right foot a shoe (Control), a cleat and a shoe (GS) and a cleat and an insole (OIC)

The main effects of foot and cycling condition along with the interaction of foot x cycling condition were found to be significant ($p<0.01$). The left foot ($61.2\pm7.3$ kPa) yielded a significantly higher peak pressure than the right foot ($44.3\pm2.9$ kPa). (FIG. 10) A Tukey's HSD post hoc was performed to analyze the simple effect of cycling condition within foot (FIG. 10). Within the left foot, cycling condition did not significantly alter peak pressure. Peak pressure for the right foot was lower ($p<0.01$) in the OIC condition ($29.5\pm2.5$ kPa) than GS ($35.8\pm1.4$ kPa) which was lower ($p<0.01$) than C ($67.7\pm7.3$ kPa). (FIG. 10)

The main effects of foot and cycling condition along with the interaction of foot x cycling condition were found to be significant ($p<0.01$). The left foot ($59.4\pm2.4$ kPa) yielded a significantly lower peak pressure than the right foot ($74.0\pm3.3$ kPa). (FIG. 10) A Tukey's HSD post hoc was performed to analyze the simple effect of cycling condition within foot. Peak pressure for the left foot Control condition ($44.3\pm2.3$ kPa) was lower ($p<0.01$) than either the GS ($60.4\pm3.0$ kPa) or OIC ($60.9\pm2.7$ kPa). Peak pressure for the right foot was lower ($p<0.01$) in the Control condition ($56.9\pm2.3$ kPa) than OIC ($74.8\pm3.8$ kPa) which was lower ($p<0.01$) than GS ($91.2\pm6.0$ kPa). (FIG. 10)

The main effects of foot and cycling condition along with the interaction of foot x cycling condition were found to be significant ($p\leq0.01$). The left foot ($70.1\pm5.1$ kPa) yielded a significantly higher total peak pressure than the right foot ($73.4\pm6.0$ kPa). A Tukey's HSD post hoc was performed to analyze the simple effect of cycling condition within foot (FIG. 10). Within the left foot, cycling condition did not significantly alter peak pressure. Peak pressure for the right foot was lower ($p<0.01$) in both the Control condition ($73.4\pm6.0$ kPa) and OIC ($74.8\pm3.8$ kPa) than the GS ($91.2\pm6.0$ kPa).

Figure 11:
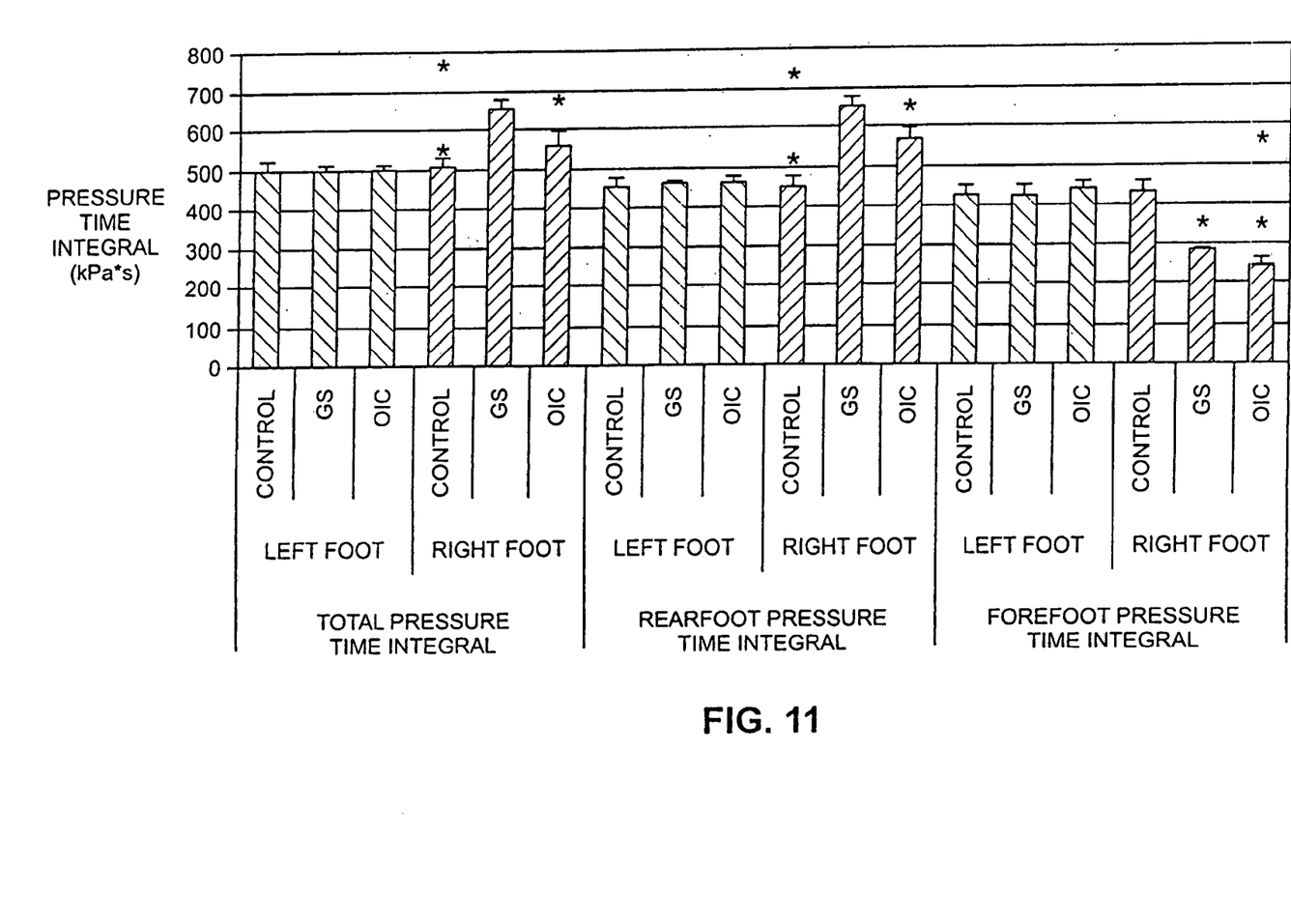
FIG. 11 is a bar graph of the results of a study showing a comparison of the pressure time integral of a left foot and a right foot of participants wearing a shoe on their left foot and on their right foot a shoe (Control), a cleat and a shoe (GS) and a cleat and an insole (OIC).
Figure 12:
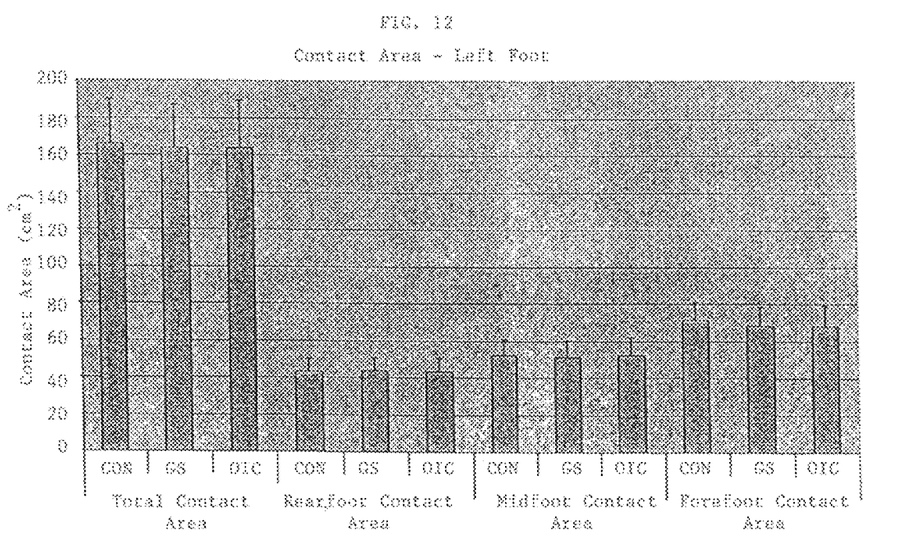
FIG. 12 is a bar graph of the results of a second study showing a comparison of the contact area of the forefoot of participants wearing on their left foot a shoe (Control), a cleat and a shoe (GS) and a cleat and an insole (OIC).
Figure 13:
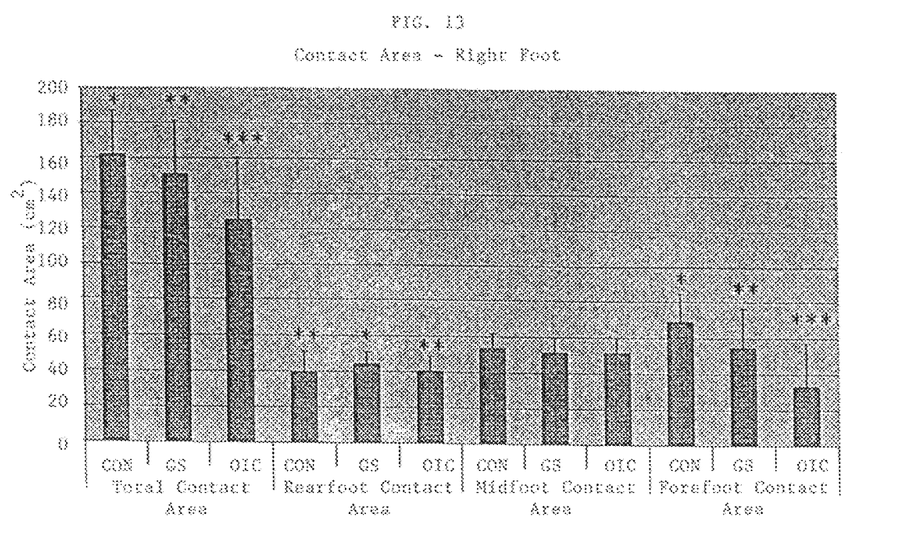
FIG. 13 is a bar graph of the results of a second study showing a comparison of the contact area of the forefoot of participants wearing on their right foot a shoe (Control), a cleat and a shoe (GS) and a cleat and an insole (OIC).
Figure 14:
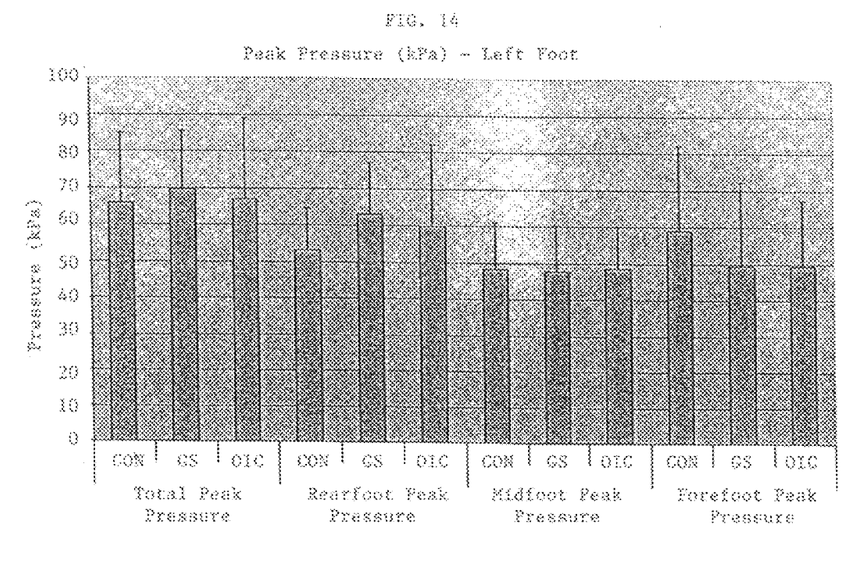
FIG. 14 is a bar graph of the results of a second study showing a comparison of the peak pressure of a left foot of participants wearing a shoe on their left foot (Control), a cleat and a shoe (GS) and a cleat and an insole (OIC).
Figure 15:
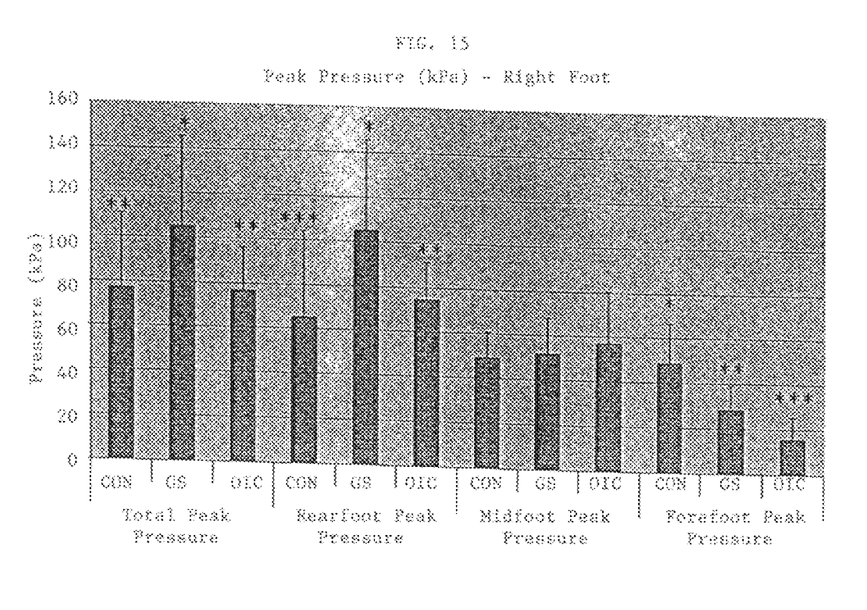
FIG. 15 is a bar graph of the results of a second study showing a comparison of the peak pressure of a right foot of participants wearing a shoe on their right foot (Control), a cleat and a shoe (GS) and a cleat and an insole (OIC).
Figure 16:
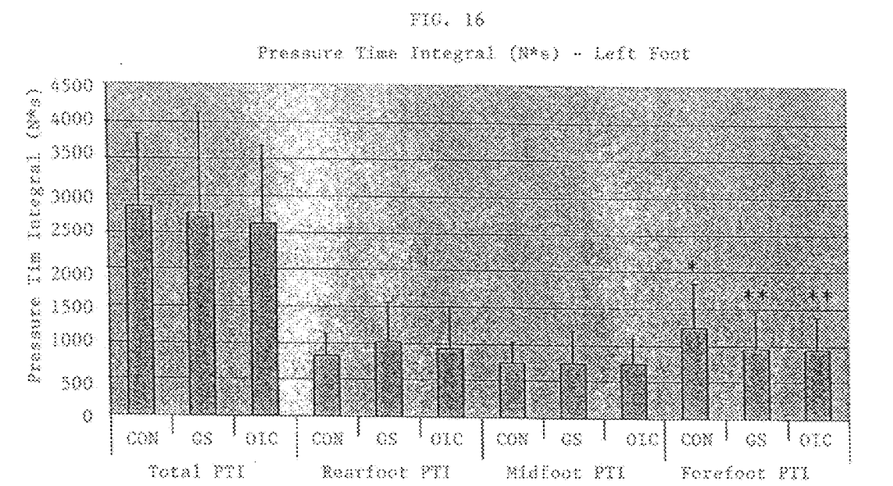
FIG. 16 is a bar graph of the results of a second study showing a comparison of the pressure time integral of a left foot of participants wearing a shoe on their left foot (Control), a cleat and a shoe (GS) and a cleat and an insole (OIC).
Figure 17:
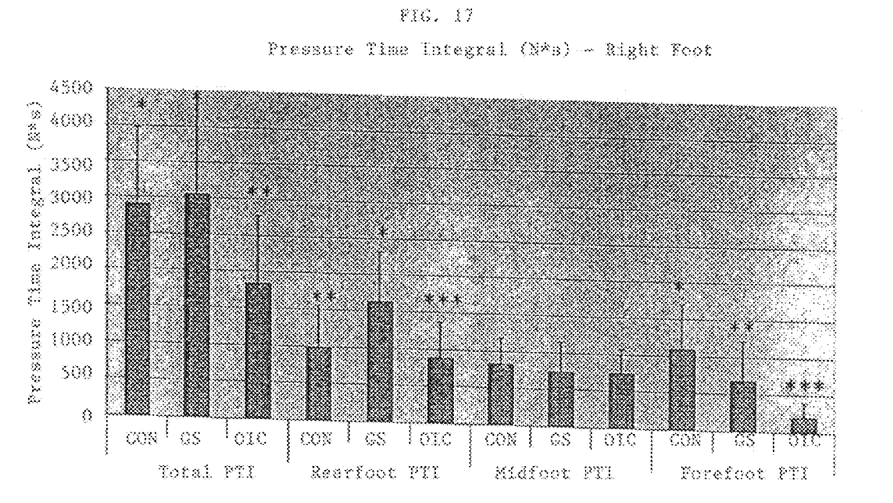
FIG. 17 is a bar graph of the results of a second study showing a comparison of the pressure time integral of a right foot of participants wearing a shoe on their right foot (Control), a cleat and a shoe (GS) and a cleat and an insole (OIC).

The main effects of foot and cycling condition along with the interaction of foot x cycling condition were found to be significant ($p<0.01$. $p=0.027$. $p<0.01$). The left foot ($407\pm30.1$ kPa*s) yielded a significantly higher pressure-time integral than the right foot ($315\pm15$ kPa*s). (FIG. 11) A Tukey's HSD post hoc was performed to analyze the simple effect of cycling condition within foot. Within the left foot, cycling condition did not significantly alter the pressure-time integral. The pressure-time integral for the right foot was lower ($p<0.01$) in the OIC condition ($246\pm21$ kPa*s) than GS ($281\pm14$ kPa*s) which was lower ($p<0.01$) than Control ($417\pm28$ kPa*s). (FIG. 11)

The main effects of foot and cycling condition along with the interaction of foot x cycling condition were found to be significant (p<0.01). The left foot (459±13 kPa*s) yielded a significantly lower pressure-time integral than the right foot (548±18 kPa). (FIG. 11) A Tukey's HSD post hoc was performed to analyze the simple effect of cycling condition within foot (FIG. 11). Within the left foot, cycling condition did not significantly alter the pressure-time integral. The pressure-time integral for the right foot was lower (p<0.01) in the Control condition (452±24 kPa*s) than OIC (553±31 kPa*s) which was lower (p<0.01) than GS (637±27 kPa*s). (FIG. 11)

The main effects of foot and cycling condition along with the interaction of foot x cycling condition were found to be significant (p≦0.01. p=0.017. p<0.01). The left foot (492±16 kPa*s) yielded a significantly lower pressure-time integral than the right foot (564±20 kPa*s). A Tukey's HSD post hoc was performed to analyze the simple effect of cycling condition within foot (FIG. 11). Within the left foot, cycling condition did not significantly alter the pressure-time integral. The pressure-time integral for the right foot was lower (p<0.01) in the Control condition (502±24 kPa*s) than OIC (553±31 kPa*s) which was lower (p<0.01) than GS (637±27 kPa*s). (FIG. 11)

The results of this study suggest that a relatively simple modification to cycling foot gear may significantly reduce the peak plantar pressure while cycling. The use of the foot gear 10 resulted in significant reductions in forefoot plantar peak pressure, contact area, and pressure time integral. The advantages of using the foot gear were enhanced by the concomitant use of an offloading insole in the OIC condition as compared to the GS condition that used standard gym shoes in collaboration with the cleat. The reduction in forefoot variables was found to be stable during exercise as evidenced by the insignificant effect of sample time. Additionally, the use of the foot gear did not appear to impede performance significantly as evidenced by the lack of change in MHR % across the three cycling conditions. These results suggest that an exercise program utilizing the foot gear may be safely implemented in patients with diabetic foot ulcers.

The use of the foot gear resulted in significantly lower forefoot contact area, peak pressure, and pressure-time integral over the athletic shoe condition. This was achieved without significant changes in exercise intensity as measured by percentage of age-predicted maximum heart rate. These properties appear desirous for instituting exercise programs in diabetic patients with neuropathic foot ulcers. By amending the current diabetic foot ulcer treatment paradigm to include an exercise regimen, health care professionals may help address the observed lower self-reported mental health status in these patients and may actually improve healing via improved immunity, blood sugar control, lipid and blood pressure profiles with subsequent angiogenesis.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

We claim:

1. An extremity stress reducing modality for a human subject having an extremity, the extremity having an uninjured portion and an injured portion, the modality comprising:
   a frame having a connecting member for removably connecting the frame to an extremity of a human subject;
   a cleat attached to a distal end of the frame for supporting a portion of the extremity of the human subject and having a top surface, a bottom surface and opposed lateral edges, the top surface for engaging the uninjured portion but not the injured portion, the, injured portion being free from any contact with the frame; and
   an attachment member on the bottom surface is adapted to directly attach the frame to a portion of a separate external moveable resistance mechanism on equipment to provide exercise for the human subject.

2. The modality of claim 1 wherein the frame has a pair of spaced vertical arms extending from opposed lateral edges of the support member, the cleat being dimensioned to support a rearfoot portion of a human subject but not a forefoot portion of a human subject and the vertical arms are dimensioned to extend along a length of a leg of the human subject, the support member being so dimensioned so as not to extend past a center of the foot of the human subject.

3. The modality of claim 1 wherein the attachment member either releasably connects or fixedly connects the frame to the separate external resistance mechanism.

4. A method for speeding up the healing of a cutaneous ulceration on an extremity of a patient by increasing angiogenesis and increasing a tissue temperature surrounding the cutaneous ulceration while mitigating direct pressure to the cutaneous ulceration, the method including the steps of:
   providing the patient with the extremity stress reducing modality of claim 1; and
   causing the patient to perform resistance-providing exercises using a separate external resistance device while wearing the extremity stress reducing modality.

5. The modality of claim 1, wherein said pair of vertical arms extend vertically not beyond a calf of the human subject.

6. A foot gear for offloading a forefoot of a human subject during a resistance exercise comprising:
   a cleat dimensioned to support a rearfoot of a human subject and to allow a forefoot of the subject to protrude freely with no fixed base beneath the forefoot, the forefoot being free from any contact with the frame;
   a leg support portion adapted to receive a leg of the subject, the leg support portion including a pair of spaced vertical arms connected to opposed lateral edges of the cleat so as (a) to extend upwardly past sides of an ankle of a human subject and terminating adjacent sides of a calf of a human subject and (b) to support the ankle at approximately 90 degrees to the foot gear;
   a support member on the foot gear for securing the foot gear to the leg of the subject; and
   an attachment member on a bottom surface of the cleat to directly to attach the frame to a portion of a separate external moveable resistance mechanism on equipment to provide exercise for the human subject.

7. The foot gear of claim 6 wherein the attachment member either releasably attaches or fixedly attaches the foot gear to the separate external resistance mechanism.

8. The foot gear of claim 6 further comprising an insole insert formed on an inside portion of the cleat, and both the insole insert and the cleat being so dimensioned as to not extend past a middle of the foot of the human subject.

9. The foot gear of claim 8 wherein the insole insert is an orthotic.

10. The foot gear of claim 6, wherein said leg support portion extends vertically not beyond a calf of the human subject.

11. An extremity stress reducing modality assembly for a foot of a human subject comprising:
- a frame having a connecting member for removably connecting the frame to a foot of a human subject;
- a cleat on the frame for engaging a rearfoot portion of the foot while leaving a forefoot portion of the foot unsupported;
- a separate external resistance member on equipment to provide exercise for the human subject and being under tension and capable of rotational or translational motion; and
- an attachment member on the cleat for directly attaching the frame to a portion of the separate external moveable resistance member.

12. The assembly of claim 11 wherein the attachment member either releasably attaches or fixedly attaches the frame to the separate external resistance mechanism.

13. The assembly of claim 11 wherein the separate external resistance mechanism is placed under tension by a member selected from the group consisting of a weight, a spring, a band, a flexible arm, a weighted fly wheel, a fan wheel, a piston, a gear and a friction shuttle.

14. The assembly of claim 11 wherein the separate external resistance member is a pedal of a bicycle.

15. The assembly of claim 14 wherein the bicycle is a stationary bicycle.

16. A method for using an extremity stress reducing modality for a human subject having an extremity having an injured portion and an uninjured portion to perform resistance-providing exercises in order to aid healing of the injured portion by increasing angiogenesis and increasing a tissue temperature surrounding the injured portion while mitigating direct pressure to the injured portion, the method comprising:.
- providing a frame having a connecting member for removably connecting the frame to an extremity of a human subject, a cleat on the frame for engaging the uninjured portion but not the injured portion, the injured portion being free from any contact with the frame, and an attachment member on the cleat for attaching the frame to a portion of a separate external moveable resistance mechanism;
- providing a separate external resistance device having a resistance member on equipment to provide exercise for the human subject and being under tension and is moveable upon application of pressure to move rotationally or translationally;
- connecting the frame to the extremity of a human subject with the uninjured portion of the extremity being supported by the cleat and the injured portion of the extremity being free from any contact with the frame;
- attaching the frame to the resistance member; and
- causing the separate external resistance device to move rotationally or translationally.

17. The method of claim 16 wherein the extremity is a foot having an injury at a forefoot portion of the foot.

18. The method of claim 17 wherein the injury is a cutaneous ulceration.

19. The method of claim 18 wherein the frame has a leg support portion adapted to receive a leg of the subject, the leg support portion including a pair of spaced vertical arms connected to opposed lateral edges of the support so as (a) to extend upwardly past sides of an ankle of the human subject and terminating adjacent sides of a calf of the human subject and (b) to support the ankle at approximately 90 degrees to the vertical arms; and
- a leg securing member on the frame for securing the frame to the leg of the subject.

20. The method of claim 19 wherein the leg securing member is selected from straps, zippers, laces, buttons, buckles, clasps, hooks, hooks and loops, and snaps.

21. The method of claim 19, wherein said leg support portion extends vertically not beyond a calf of the human subject.

22. The method of claim 18 wherein the exercise speeds the healing of the cutaneous ulceration by increasing angiogenesis and increasing a tissue temperature surrounding the cutaneous ulceration while mitigating direct pressure to the cutaneous ulceration.

* * * * *